(12) United States Patent
Kaiser

(10) Patent No.: US 8,460,562 B2
(45) Date of Patent: Jun. 11, 2013

(54) COCHLEAR IMPLANT ASSEMBLY

(75) Inventor: Thomas Kaiser, Boulder, CO (US)

(73) Assignee: Cochlear Limited, Macquarie University, NSW (AU)

( * ) Notice: Subject to any disclaimer, the term of this patent is extended or adjusted under 35 U.S.C. 154(b) by 1167 days.

(21) Appl. No.: 12/096,461

(22) PCT Filed: Dec. 6, 2006

(86) PCT No.: PCT/AU2006/001855
§ 371 (c)(1),
(2), (4) Date: Oct. 6, 2008

(87) PCT Pub. No.: WO2007/065216
PCT Pub. Date: Jun. 14, 2007

(65) Prior Publication Data
US 2009/0165921 A1 Jul. 2, 2009

(30) Foreign Application Priority Data
Dec. 6, 2005 (AU) .................................. 2005906847

(51) Int. Cl.
*H01B 13/00* (2006.01)
(52) U.S. Cl.
USPC .................... 216/13; 216/15; 216/20
(58) Field of Classification Search
USPC .............................................. 216/13, 15, 20
See application file for complete search history.

(56) References Cited

U.S. PATENT DOCUMENTS

| | | | |
|---|---|---|---|
| 4,762,135 A | | 8/1988 | van der Puije et al. |
| 5,324,322 A | * | 6/1994 | Grill et al. ...................... 607/118 |
| 5,545,219 A | * | 8/1996 | Kuzma ............................. 623/10 |
| 2004/0147992 A1 | * | 7/2004 | Bluger et al. ................. 607/116 |
| 2004/0220651 A1 | * | 11/2004 | Kuzma et al. ................. 607/137 |
| 2004/0256146 A1 | * | 12/2004 | Frericks et al. ............... 174/254 |
| 2006/0195143 A1 | * | 8/2006 | McClure et al. .................. 607/2 |
| 2007/0123963 A1 | * | 5/2007 | Krulevitch .................... 607/115 |

FOREIGN PATENT DOCUMENTS

| WO | 02089907 | 11/2002 |
|---|---|---|
| WO | 2004035133 | 4/2004 |

OTHER PUBLICATIONS

International Search Report. PCT/AU2006/001855. Filed Dec. 6, 2006; mailed Jul. 26, 2007.

* cited by examiner

*Primary Examiner* — Binh X Tran
(74) *Attorney, Agent, or Firm* — Kilpatrick, Townsend & Stockton, LLP.

(57) ABSTRACT

A method of forming electrode structures comprising a plurality of electrode pads and a plurality of electrically conducting wires extending from the electrode pads. The method comprises coating an electrode structure with a relatively electrically insulating material, arranging each of the electrode pads in a first arrangement; arranging the wires relative to each other to provide a sufficient gap of separation between neighboring wires; securing the wires to a remotely positioned anchor member to preserve a gap of separation between neighboring wires, and applying a coating of relatively electrically insulating material to the electrode structure.

77 Claims, 11 Drawing Sheets

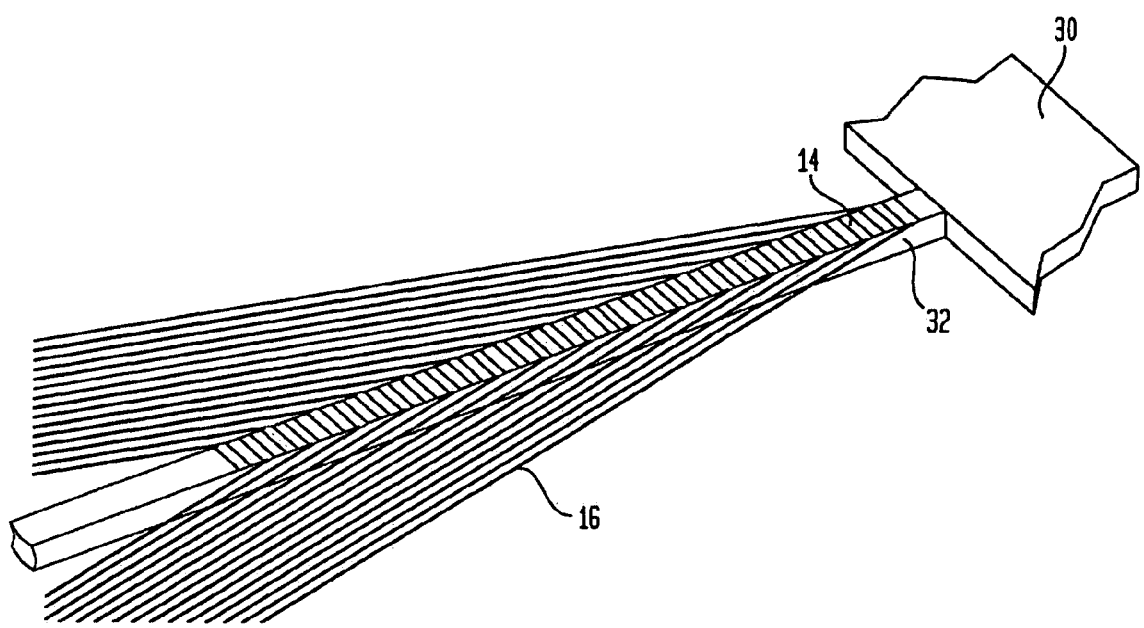

COCHLEAR IMPLANT ASSEMBLY

CROSS-REFERENCE TO RELATED APPLICATIONS

The present application is a National Stage application of PCT/AU2006/001855 entitled "Cochlear Implant Assembly", filed on Dec. 6, 2006. The present application also claims priority from Australian Provisional Patent Application No 2005906847 filed on 6 Dec. 2005. The above patent applications are hereby incorporated by reference herein.

BACKGROUND

1. Field of the Invention

The present invention relates generally to the field of forming electrode structures for electrical products and, more specifically, forming respectively insulated electrode structures that may be used in electrode arrays.

2. Related Art

In many electrical devices, particularly those that are manufactured on a very small scale, the manufacture of the wiring and related components is often a labor intensive and specialized craft. In particular, ensuring that the wiring and electrical connection of the various components of the systems occurs correctly is often the most expensive and labor intensive aspect of the manufacturing process. This cost is often passed on to the ultimate consumer. This is also the case when such devices need to be specifically hand-made to a specification as often the availability of the device is dependent upon the time taken to manufacture the device, with the time taken being difficult or impossible to expedite.

This is often particularly the case in the field of medical implants and electrical devices that are implanted in the body. Such devices may include, for example, stimulating devices such as pacemakers, cochlear implants, FES stimulators, and the like; recording devices such as neural activity sensors and the like; implantable cables which connect implantable devices to other implantable devices; diagnostic devices capable of carrying out in vivo analysis of body parameters, and other types of implantable devices not yet contemplated.

In such devices, it is often desirable to minimize the size to ensure that they are minimally invasive upon implantation. As a result, in such instances, the electronic wiring and connections need also to be relatively very small. As such, manufacturing such devices to ensure that they are reliable and sturdy is a specialized art, requiring much time and expense.

Current techniques for the manufacture of electrode arrays for cochlear implant systems, in particular, are relatively highly labor intensive. This is primarily due to the intricate nature of the array and the very small dimensions of the array necessary to allow it to be inserted in the scala tympani of the human cochlea. Being an implantable device capable of delivering and applying electrical currents to surrounding tissue, there is a need to ensure that the elements of the array are electrically isolated from each other to avoid short circuits and the like which may greatly diminish the benefits of such a device, as well as have the potential to cause pain and discomfort to the recipient.

SUMMARY

According to one embodiment of the present invention, a method of coating an electrode structure with an electrically insulating material, the electrode structure is provided. The method comprises a plurality of electrode pads and a plurality of electrically conducting wires, at least one wire extending from at least one of the electrode pads. The method comprises arranging each of the electrode pads in a first arrangement; arranging the wires relative to each other to provide a gap of separation between neighboring wires; securing the wires to a frame member to preserve the gap of separation between neighboring wires; and applying a coating of electrically insulating material to the electrode structure, wherein the gap is sufficient to enable the application of the coating of electrically insulating material to all surfaces of the wires without webbing between adjacent wires.

According to another embodiment of the present invention, a method for of forming an electrode structure comprising a plurality of electrode pads and a plurality of electrically conducting wires extending from the electrode pads, for use in an electrode array of an implantable medical device is provided. The method comprises attaching a sheet of conductive material to a sheet of carrier material; working the sheet to remove predetermined portions thereof to form a plurality of electrode pads of conductive material supported on an electrode support of carrier material, a frame member; and a plurality of wires of relatively electrically conductive material, at least one wire connecting an electrode pad to the frame member; coating the worked sheet with an electrically insulating material; and removing the electrode support.

BRIEF DESCRIPTION OF THE DRAWINGS

By way of example only, preferred embodiments of the invention are now described with reference to the accompanying drawings, in which:

FIG. 3a is a perspective view of an electrode structure supported on an electrode support in accordance with one embodiment of the present invention;

DETAILED DESCRIPTION

Aspects of the present invention generally relate to the field of forming electrode structures for electrical products. In particular, embodiments of the present invention are directed to forming respectively insulated electrode structures that may be used in electrode arrays. Such as arrays may be used for sensors, including biosensors, and implantable devices, such as an implantable recording or stimulating electrodes or pads for use in the body.

Figure 1:
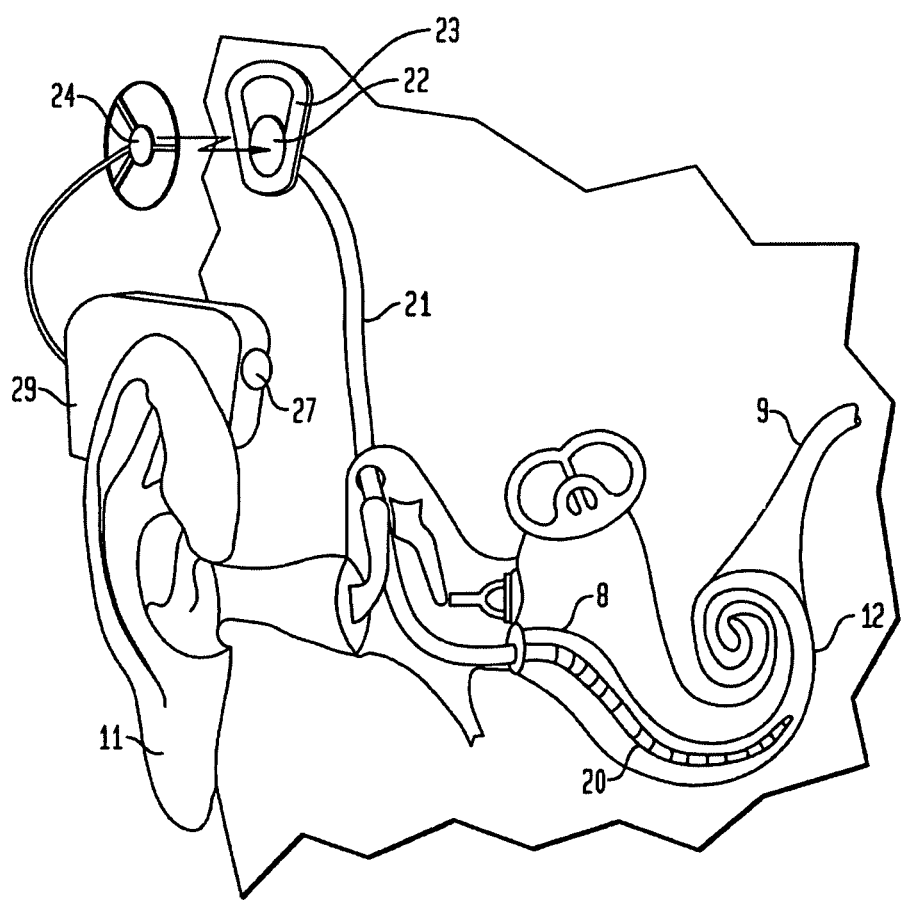
FIG. 1 is a perspective view of a cochlear implant system in which embodiments of the present invention may be advantageously implemented.

One type of known cochlear implant system with reference to FIG. 1. It will be appreciated that whilst the present invention will be discussed in relation to a cochlear implant system, the present invention is equally applicable to a variety of implantable devices, such as biosensors, pacemakers, FES stimulators and neurostimulators.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body or clothing. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

Figure 2:
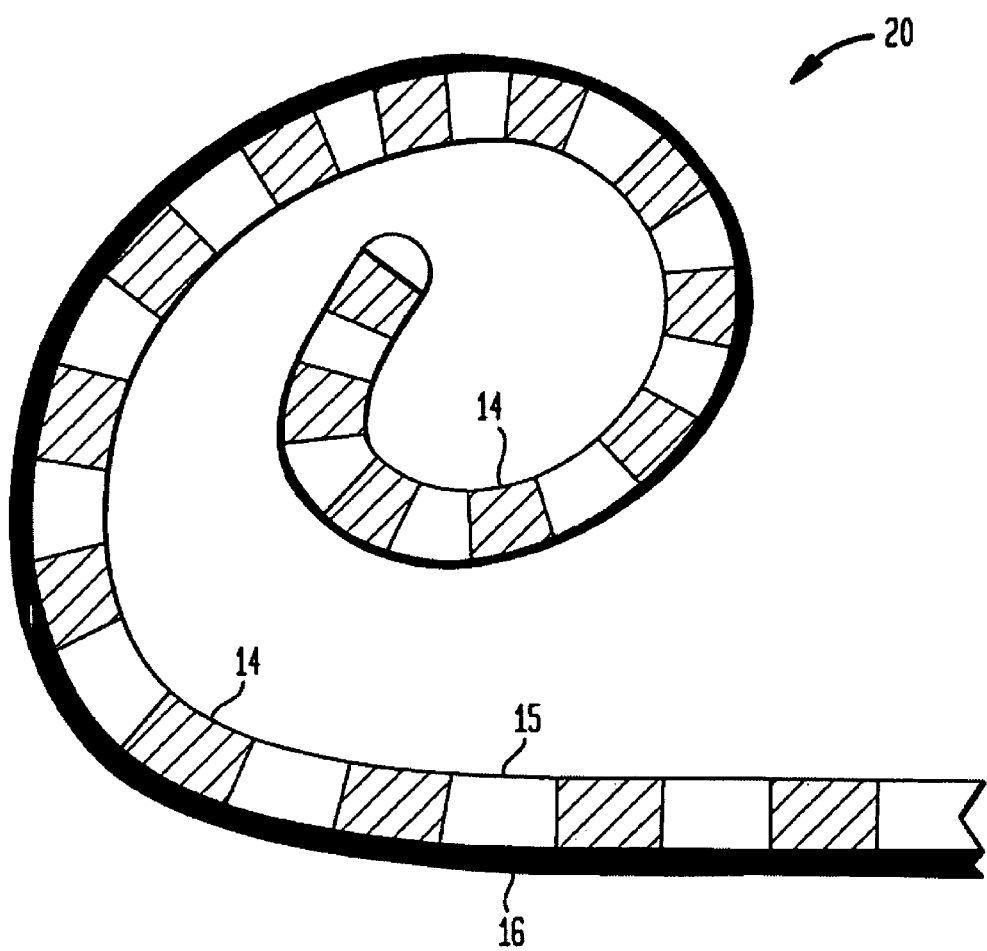
FIG. 2 is a side view of an electrode array suitable for use with the cochlear implant system of FIG. 1.

An example of an electrode array suitable for use with such a cochlear implant system is shown in relation to FIG. 2. In this arrangement, the electrode array 20 comprises a flexible carrier member 15 moulded in a spirally-curved configuration. The carrier member 15 may be made from a material such as silicone, which has the appropriate flexibility properties to enable the electrode array to assume a desired shape to facilitate insertion. A plurality of electrode pads 14 are arranged at dedicated intervals along the length of the inner wall of the carrier member 15 with each electrode pad 14 being connected to the stimulator unit 22 via a wire or conductor 16 which extends within the outer wall of the carrier member 15. The number of electrode pads 14 present in the electrode array 20 can vary. In one form, there may be 2-2 electrodes positioned along the length of the carrier member 15, which may be 20-30 mm in length. In this regard, each of the electrode pads 14 are connected to the implanted receiver and stimulator unit 22 via a wire 16, thereby resulting in the electrode array 20 housing 22 individual wires 16, each of which are electrically isolated from each other to avoid shorting between the wires 16, and incorrect stimulation of the nerves.

Typically, prior to implantation into the cochlea the electrode array 20 is straightened by the presence of a stylet or other straightening means (not shown) which is received within a lumen formed in the carrier member 15. Upon removal of the stylet, the electrode array 20 is able to adopt the configuration as shown in FIG. 2 to conform to the shape of the inner wall of the cochlea such that the electrodes 14 are positioned to deliver appropriate electrical stimulation to the desired nerve cells within the cochlea. It will be appreciated that the degree of curvature of the depicted electrode array is to be taken as illustrative only, and as the electrode curves during implantation the wires 16 also undergo a degree of curvature.

The electrode array 20 can be constructed in a variety of ways. In this regard, it should be appreciated that the structure of the electrode array 20 is substantially provided by the electrode pads 14 and the associated wires 16 which are encapsulated within the flexible carrier 15. The electrode pads 14 and corresponding wires 16 may be formed by either a one-piece or two-piece construction method, and the present invention will now be described in relation to both these methods.

A one-piece construction method for creating the electrode pads 14 and associated wires 16 is described in International Patent Application PCT/AU02/00575 (WO 02/089907), the content of which is incorporated herein by reference. In the method described, a foil of conductive material is applied to a carrier or substrate, and portions of the foil and carrier are removed to create a pattern of electrode pads and associated wires. Following creation of a plurality of one-piece electrode pads and associated wires, the top surface of the pads and wires are sprayed or otherwise applied with a layer of relatively electrically insulating and resiliently flexible material, and the carrier or substrate is then removed. The individual one-piece electrode pads and wires are retained together via the layer of insulating and resiliently flexible material, and the areas of foil removed are also filled with an insulating material. The undersurface of the electrode pads and wires are then coated with a layer of insulating and resiliently flexible material, and the region of the electrode pads is preferably masked to ensure they remain uncovered to deliver electrical stimulation. The individual electrode pad and wire sets are then arranged in an appropriate jig and shaped and encapsulated in the carrier material to form the electrode array as shown in FIG. 2.

As will be appreciated, the method of insulating the individual wires from neighboring wires in the above one-piece construction method is relatively complicated and requires a number of separate insulating steps. As the wires are typically arranged in close proximity to each other, the insulating material may not individually coat each wire but rather create a "web effect" between a group of wires which may not provide total electrical isolation between wires. As a result, shorting may still occur between wires in a web, which can reduce the effectiveness of the electrical stimulation and in some instances cause discomfort to the individual. Similarly, such a "webbing" of neighboring wires increases the rigidity of the wires which can increase the overall rigidity of the electrode array, thereby reducing the ability of the array to adopt various shapes.

In order to simplify the manner in which the insulation is applied to the electrode structures in a one-piece construction method, the method of the present invention will now be described with reference to FIGS. 3a-7.

Figure 3B:
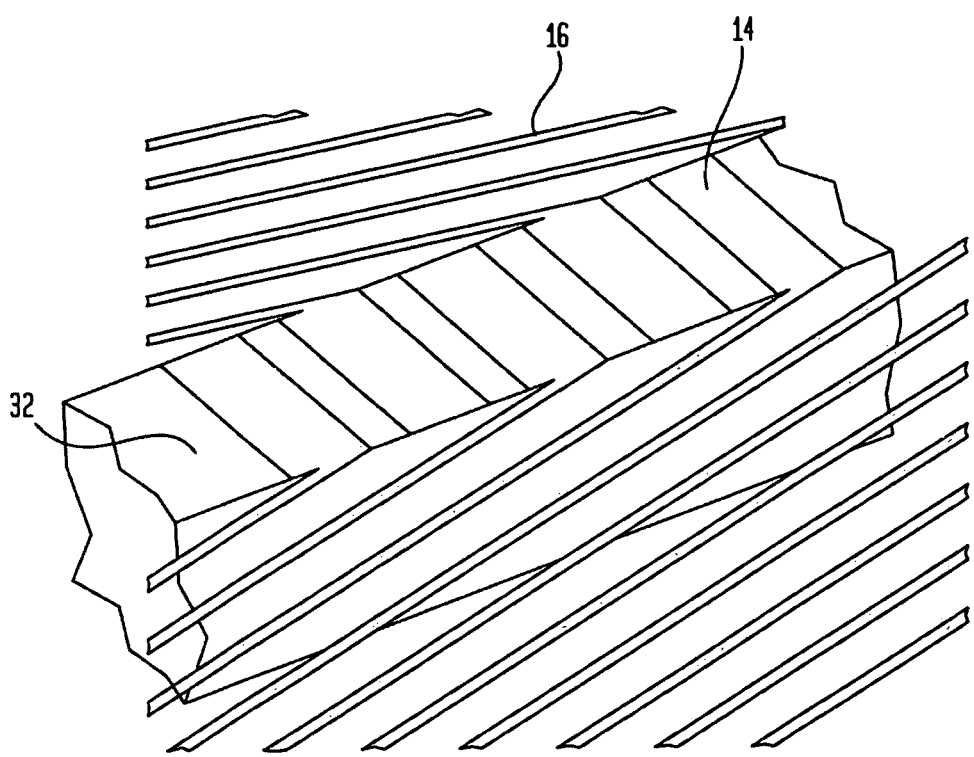
FIG. 3b is an enlarged view of a portion of FIG. 3a, showing the electrode pads arranged in an array upon an electrode support and the wires extending therefrom in an angular arrangement.

Firstly a foil of conductive material, for example platinum (Pt) or gold (Au), is applied to a carrier or substrate, for example copper (Cu), and portions of the foil and carrier are removed to create a pattern of electrode pads 14 and associated wires 16 as shown in FIG. 3a. While each pad 14 is depicted as having one wire 16 extending therefrom, it will be appreciated that one, some or all of the pads 14 could have more than one wire 16 extending therefrom. A variety of material removing methods may be employed to create the desired pattern in the material, for example using electrical discharge machining (EDM) or a variety of etching processes. The foil and substrate is then worked such that a frame 30 remains about the pattern of electrode pads 14 and wires 16 and an electrode support 32 is provided by the substrate which forms a backing for the electrode pads 14. In this regard, the electrode pads 14 remain aligned together on the electrode support 32 and the wires or conductors 16 are freed from the substrate, as is shown more clearly in FIG. 3b. Such selective etching of the substrate may be performed by masking the material with a photo resist layer prior to etching. In alternative embodiments, the electrode pads 14 are not aligned together on the electrode support 32.

In the embodiment shown, the electrode pads 14 are substantially rectangular having a pair of diametrically opposed ends which are formed parallel with the walls of the electrode support 32, which are in turn connected via a pair of opposed sides, which extend across the surface of the electrode support 32. However, it will be appreciated that other shapes of the electrode pads are possible and still fall within the scope of the present invention.

Figure 4A:
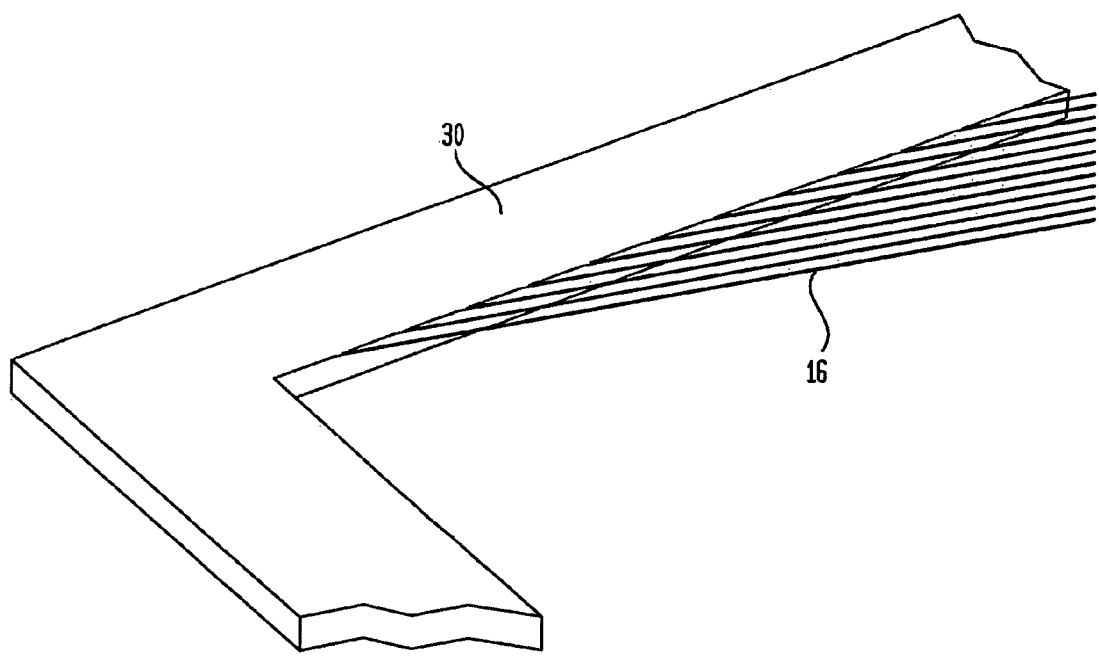
FIG. 4a is a perspective view of the wires of the electrode structure of FIGS. 3a and 3b connected to a support frame.
Figure 4B:
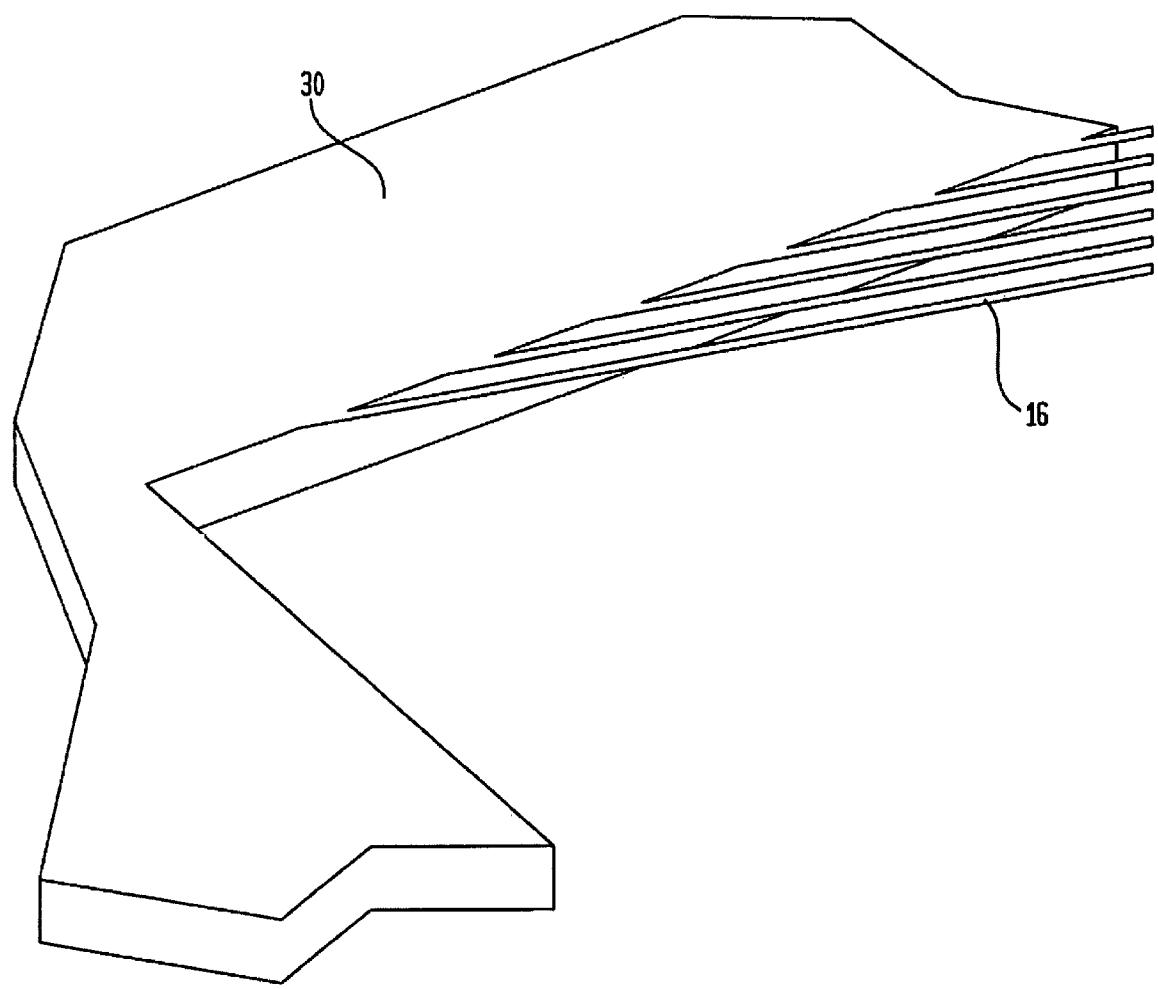
FIG. 4b is an enlarged view of a portion of FIG. 4a, showing the connection of the wires with the support frame.

As shown more clearly in FIGS. 4a and 4b, whilst the wires 16 are substantially free from the backing substrate, the distal ends of the wires 16 remain attached to the frame 30 of substrate and foil, to prevent the wires 16 from becoming tangled during handling. The wires 16 are integral with the electrode pads 14 and extend angularly from an opposing end of the pads. To facilitate sufficient separation between angularly extending wires 16, the wires are arranged to extend from alternative opposed ends of adjacent pads 14. Such an arrangement ensures that the distance between adjacent wires 16 in the structure as shown in FIGS. 3a-4b, is sufficient to enable coating of the wires 16 with a suitable electrically insulating coating without causing webbing between adjacent wires, as discussed in relation to the previous method.

In this regard, the electrode pads 14 can be masked and the entire arrangement as shown in FIGS. 3a-4b can be coated with a suitable electrically insulating material, such as parylene, including parylene N and parylene C, thereby ensuring the surfaces of the wires are fully coated and electrically isolated from each other. The coating step may be performed by vapour deposition techniques or other type of spraying or immersion techniques.

Figure 5:
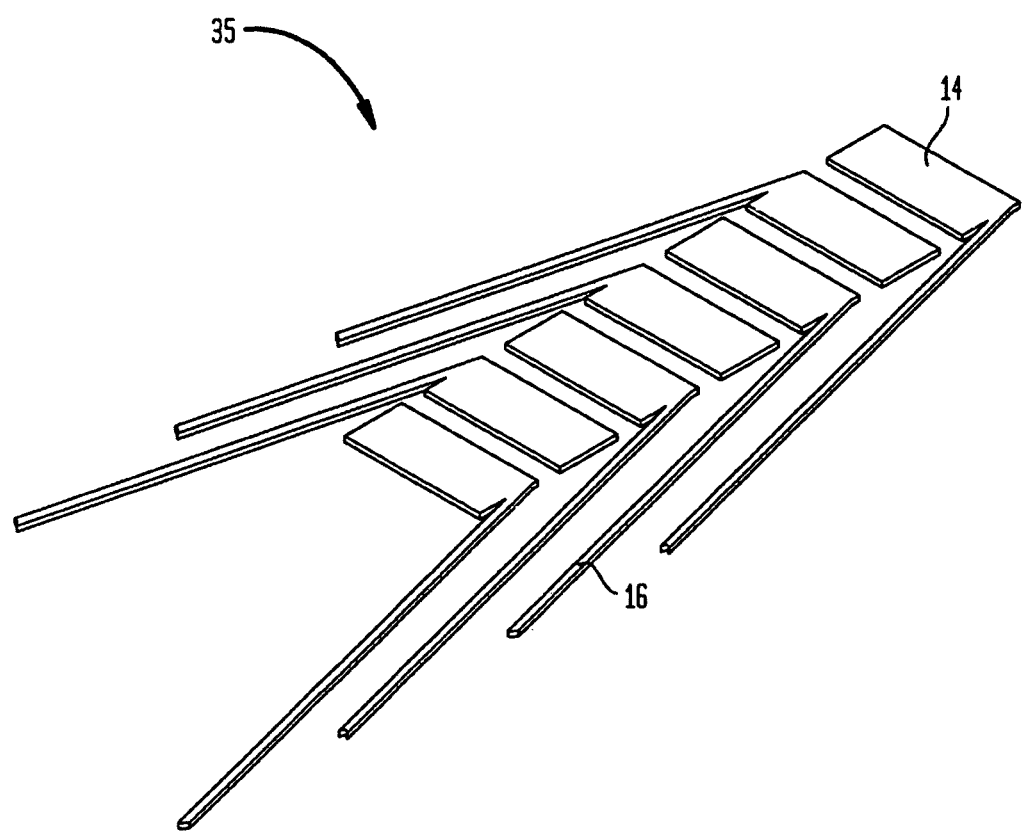
FIG. 5 is a perspective view of the electrode structure of FIGS. 3a-4b following removal of the electrode support.

Following coating of the arrangement, the remainder of the substrate is removed, thereby removing the electrode support 32 and part of the frame portion 30. The coating may need to be selectively stripped to enable etching of the substrate, and such selective stripping may be performed by a laser or hot wire, to create the electrode structure 35 made up of electrode pads and wires as shown in FIG. 5. To aid in aligning the pads 14 and associated wires 16 when the substrate is removed, a layer of thin silicone sheeting may be applied to the surface of the stimulation pads, prior to removal of the substrate.

The ends of the wires 16 are separated from the foil portion of the frame 30 by laser cutting or by other suitable methods. The electrode structure 35 may be then placed in an assembly jig and manipulated to form an electrode array such as is shown in FIG. 2. In this regard however, all sides of each of the wires 16 are each individually coated with insulating material in one step thereby providing greater electrical isolation between neighbouring wires in the electrode array 20.

Figure 6:
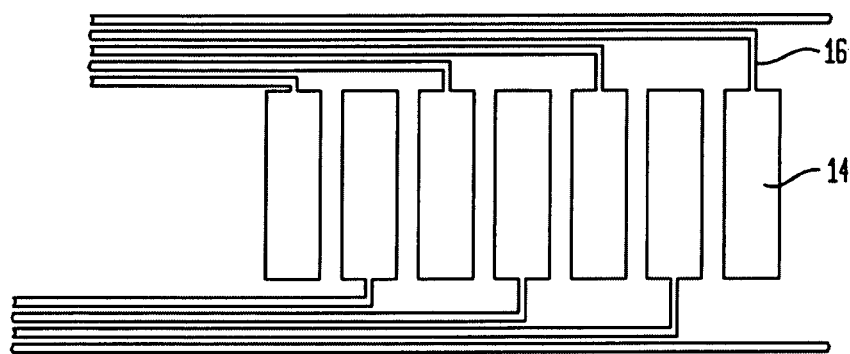
FIG. 6 is a plan view of the electrode pad and wire arrangement of the electrode structure in accordance with an alternative embodiment of the present invention.
Figure 7:
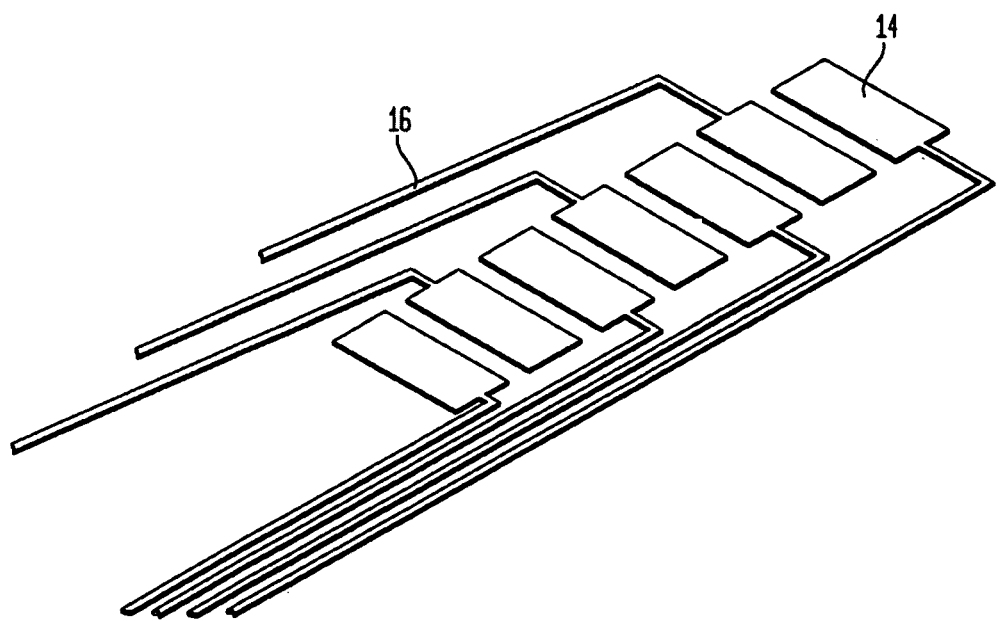
FIG. 7 is a perspective view of a clamping arrangement for securing the wires in accordance with the embodiment of FIG. 6.

In an alternative embodiment, the structure of the electrode pads 14 and associated wires 16 may be arranged such that the wires 16 run parallel to the arrangement of the pads 14 as is shown in FIG. 6. In this arrangement, in order to ensure that the spacing between neighboring wires is sufficient to prevent "webbing" and ensure that the electrically insulating coating can be applied to all the surfaces of the wires, prior to coating the arrangement the ends of the wires are separated from the frame 30 and raised to a different height and clamped in place, as shown in FIG. 7.

Figure 8:
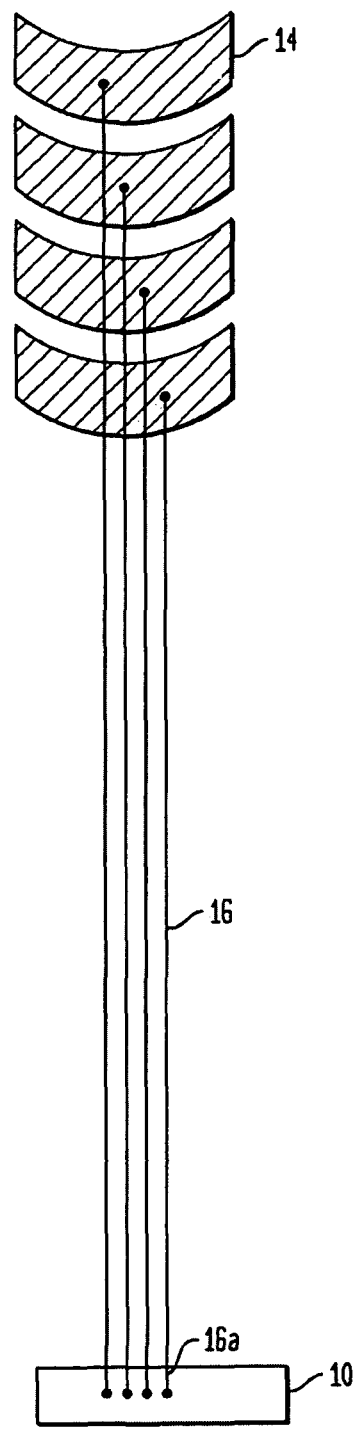
FIG. 8 is a plan view showing an electrode structure with the distal ends of the wires attached to a sacrificial member in accordance with a prior art assembly method.

A two-piece construction method for creating the electrode pads 14 and associated wires 16 is described in International Patent Application PCT/AU04/001726 (WO 2005/055363), the content of which is incorporated herein by reference. In the method described, the electrode pads 14 are separately formed by punching the desired shape of the electrode pads from a foil of conductive material, such as a foil of platinum (Pt). The electrode pads may have a variety of shapes and are removed from the foil such that they remain connected to each other. Following removal, the electrode pads 14 may be further shaped as desired and an end of an electrically conducting wire is welded to the surface of each of electrode pads. The wire is typically pre-coated with an electrically insulating material and, as such, a small portion of the electrical conducting material is removed from the ends of the wires to enable each wire to be welded to the electrode pad. Similarly, the other end 16a of each wire is also welded to a sacrificial plate 10 to ensure alignment. A portion of this process is shown in FIG. 8. Following connection of each of the wires 16 to the electrode pads and to the sacrificial plate 10, the wires can then be separated from the sacrificial plate 10 and the wires and electrode pads assembly can be placed in an appropriate jig and formed into an electrode array such as that shown in FIG. 2. In this regard, the method requires the wires 16 to be pre-coated with an appropriate insulating material, which adds to the production costs associated with manufacturing such an electrode array 20, and also requires an additional step of removing the insulating material from each of the ends of the wires, which is an additional step in the process.

Figure 9:
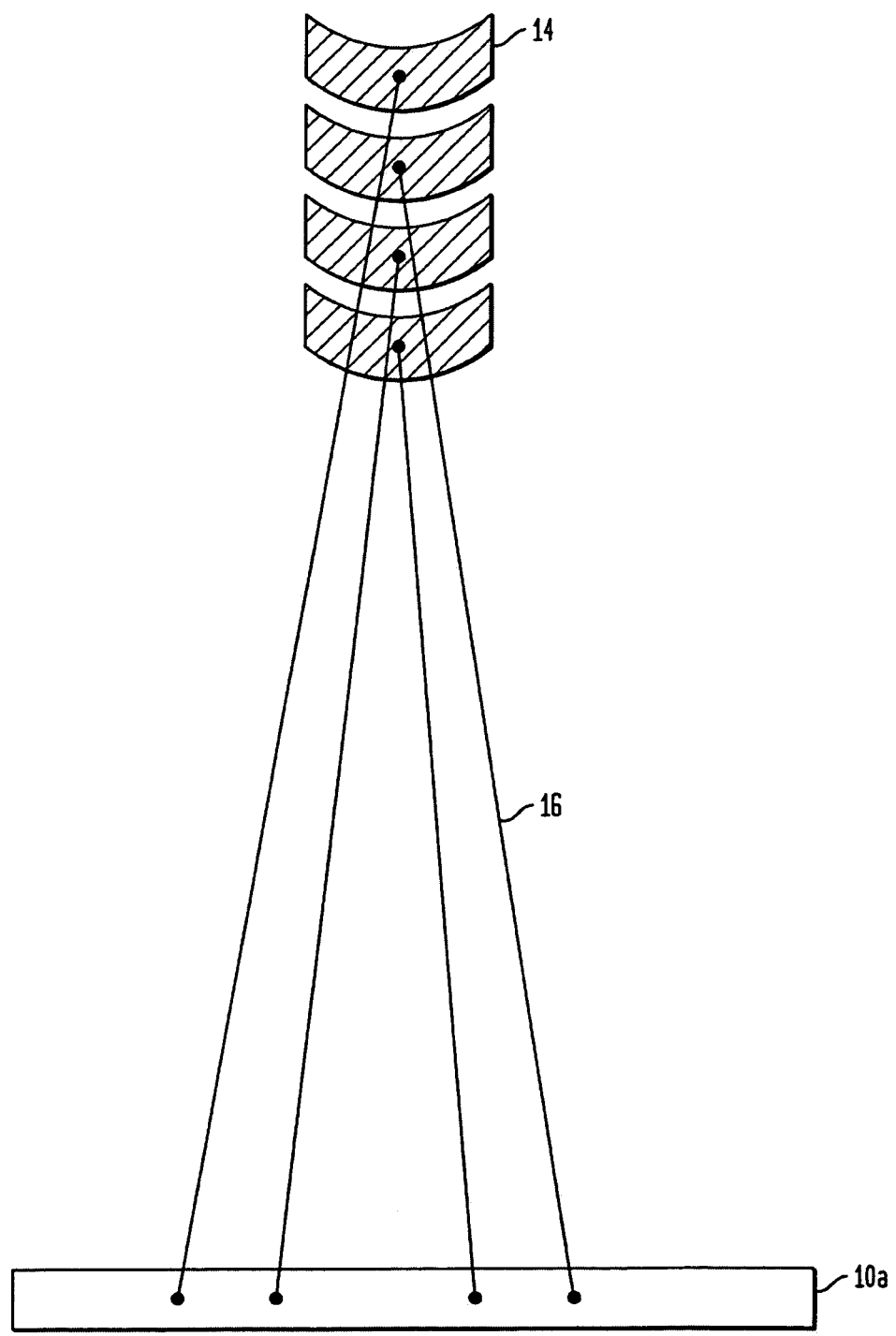
FIG. 9 is a plan view showing an electrode structure with the distal ends of the wires attached to a sacrificial member in accordance with a method of the present invention.
Figure 10:
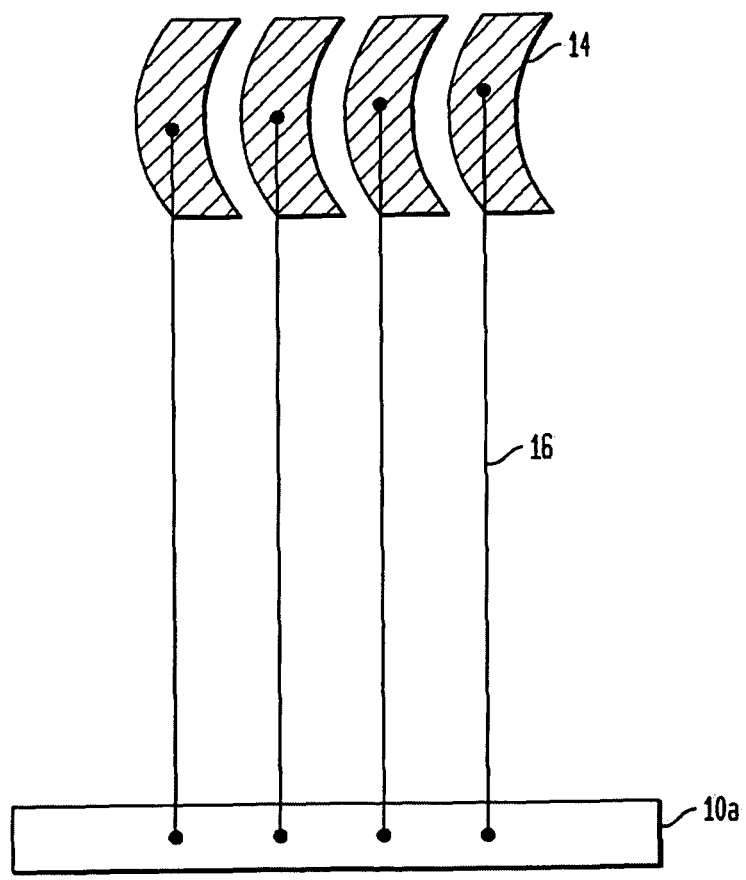
FIG. 10 is a plan view showing an electrode structure with the distal ends of the wires attached to a sacrificial member in accordance with an alternative method of the present invention.

As shown in FIGS. 9 and 10, the present invention is also applicable to electrode structures of such a two-piece construction wherein the wires 16 are not coated with an appropriate insulating material prior to assembly and a coating step is required following assembly. In the prior art arrangement shown in FIG. 8, the wires are positioned in close proximity to each other as they extend between the electrode pads 14 and the sacrificial member 10, and as such should a coating step be employed there is likelihood of "webbing" occurring between adjacent wires thereby providing rigidity to the structure and increasing the likelihood of shorting occurring between adjacent wires.

Therefore, by fixing the ends of the wires to the sacrificial plate 10a at greatly spaced intervals along the plate 10a such that distance between wires 16 is maximised, as shown in FIG. 9, it is possible to employ uncoated conducting wires and then apply a coating step to the structure prior to separating the wires 16 from the sacrificial plate 10a. Similarly, as shown in FIG. 10, the wires 16 can extend laterally from the electrode pads 14, thereby ensuring that sufficient distance is provided between adjacent wires 16 to enable individual coating of the wires 16 with an insulating coating. Further, to facilitate separation of the wires prior to the coating step, the wires may be separated from the sacrificial plate 10a and raised to a different height and clamped in place, similar to that described in relation to FIG. 7.

It will be appreciated that the coating step will typically involve coating the structure with parylene or any other type of suitable insulating material via vapour deposition methods. As such, the stimulating surfaces of the electrode pads 14 may be masked prior to coating to prevent deposits of insulating material forming thereon and reducing the effectiveness of the electrodes.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:
1. A method of coating an electrode structure with an electrically insulating material, the electrode structure com- prising a plurality of electrode pads and a plurality of electrically conducting wires, at least one of the electrically conducting wires extending from at least one of the electrode pads, the method comprising:

arranging each of the plurality of electrode pads in a first arrangement wherein the electrode pads are located in a single longitudinal row;

arranging the electrically conducting wires relative to each other such that at least some of the electrically conducting wires are adjacent one other and provide a gap of separation between adjacent electrically conducting wires and wherein the electrically conducting wires extend from alternate opposing ends or edges of adjacent electrode pads in the single longitudinal row;

securing the electrically conducting wires to a frame member to preserve said gap of separation between adjacent electrically conducting wires; and applying a coating of electrically insulating material to said electrode structure, wherein said gap is sufficient to enable said application of said coating of electrically insulating material to all surfaces of said electrically conducting wires without webbing between adjacent electrically conducting wires, and wherein all of the electrode pads in the electrode structure are located in the single longitudinal row.

2. The method of claim 1, wherein the plurality of electrode pads are arranged such that they are aligned with respect to each other.

3. The method of claim 1, wherein said plurality of electrode pads are arranged such that at least some of the respective electrode pads are unaligned with respect to each other.

4. The method of claim 1, wherein at least one of said electrode pads is substantially circular or oval in shape.

5. The method of claim 1, wherein said step of applying said coat of electrically insulating material to said electrode structure comprises one of either dip coating and spray coating.

6. The method of claim 1, wherein arranging the electrically conducting wires relative to each other to provide a gap of separation between adjacent electrically conducting wires comprises:

elevating adjacent electrically conducting wires such that they are secured to said frame member at different heights.

7. The method of claim 6, wherein securing said electrically conducting wires to said frame member comprises:

individually clamping the distal ends of each said electrically conducting wire.

8. The method of claim 1, wherein the electrode pads are substantially rectangular in shape.

9. The method of claim 8, wherein at least one electrically conducting wire is arranged to extend from a peripheral edge of at least one of the electrode pads.

10. The method of claim 9, wherein the step of arranging said wires relative to each other to provide a gap of separation between neighboring wires comprises:

extending said wires tangentially from said edge of said electrode pads.

11. The method of claim 1, wherein prior to applying the coating of electrically insulating material to the electrode structure, portions of the electrode structure are masked to prevent coating of the masked portions.

12. The method of claim 11, wherein what are to become the stimulating surfaces of the electrode pads are masked to prevent them from being coated with the electrically insulating material.

13. The method of claim 12, wherein the masking is performed by applying a suitable tape or laminar material to the surface of the electrode structure, which is later removed following the coating step.

14. The method of claim 1, wherein the step of applying the coat of relatively electrically insulating material to the electrode structure comprises:

employing vacuum deposition techniques to coat the electrode structure.

15. The method of claim 14, wherein the electrically insulating material is parylene.

16. The method of claim 15, wherein the parylene is coated on said electrode structure by vapour-phase deposition.

17. The method of claim 1, wherein said electrode pads comprise a pair of diametrically opposed ends connected by a pair of diametrically opposed sides.

18. The method of claim 17, wherein said diametrically opposed ends are shorter in length than said diametrically opposed sides of said electrode pads.

19. The method of claim 18, wherein the step of arranging said electrically conducting wires relative to each other to provide a gap of separation between adjacent electrically conducting wires comprises:

extending each of said electrically conducting wires from said electrode pads at an angle to said diametrically opposed ends of said electrode pads.

20. The method of claim 18, wherein said electrode pads are arranged in the single longitudinal row such that said diametrically opposed ends of each electrode pad are aligned with respective diametrically opposed ends of other electrode pads in said single longitudinal row.

21. The method of claim 20, wherein at least one electrically conducting wire extends from at least one of said diametrically opposed ends of at least one of the electrode pads.

22. The method of claim 1, wherein the step of securing said electrically conducting wires to a frame member comprises:

forming said electrode structure such that said distal end of each electrically conducting wire is integrally formed with said frame member.

23. The method of claim 22, wherein said frame member comprises:

a portion of said sheet of electrically conductive material and substrate.

24. The method of claim 23, wherein said frame member is in the form of a frame portion comprising a peripheral region of said sheet of electrically conductive material and substrate.

25. The method of claim 24, wherein said frame portion comprises a rectangular frame portion.

26. The method of claim 24, wherein said frame portion comprises a substantially circular or oval frame portion.

27. The method of claim 1, wherein said electrode structure is formed from a single sheet of relatively electrically conducting material.

28. The method of claim 27, wherein said single sheet of electrically conducting material is applied to a carrier or substrate to facilitate handling of said electrically conductive material to form said electrode structure.

29. The method of claim 28, wherein said electrically conductive material is a foil of relatively electrically conductive material.

30. The method of claim 29, wherein said electrically conductive material comprises one or more of platinum or gold.

31. The method of claim 28, wherein said substrate comprises a sheet of copper.

32. The method of claim 28, wherein said electrode structure is formed by selectively removing selected parts of said electrically conductive material and said carrier or substrate.

33. The method of claim 32, wherein said electrode pads and associated electrically conducting wires are formed integral with each other.

34. The method of claim 33, wherein each said electrically conducting wire has a proximal end and a distal end.

35. The method of claim 34, wherein said proximal end of each electrically conducting wire is connected to said electrode pad, and said distal end of each electrically conducting wire is secured to said frame member.

36. The method of claim 35, wherein said connection of said proximal end of said electrically conducting wire with said electrode pad is an integral connection.

37. The method of claim 32, wherein said selected parts of said electrically conductive material and said substrate are removed by one or more of either electrical discharge machining, etching and cutting.

38. The method of claim 37, wherein a portion of said substrate acts as an electrode support upon which said electrode pads are arranged.

39. The method of claim 38, wherein the step of arranging said electrode pads in a first arrangement comprises:
removing selected parts of said electrically conductive material to form said electrode pads; and
retaining a portion of said substrate as a support for said electrode pads.

40. The method of claim 39, wherein said electrically conducting wires are formed such that they are free from said substrate.

41. The method of claim 1, wherein said electrode pads and associated electrically conducting wires are each formed separately.

42. The method of claim 41, wherein said electrode pads are formed from a sheet of conductive material.

43. The method of claim 42, wherein said sheet of conductive material is worked to create a desired shape of said electrode pads.

44. The method of claim 43, wherein said sheet of conductive material is punched, or cut or otherwise abraded to create said electrode pads.

45. The method of claim 41, wherein said proximal end of said electrically conducting wires are attached to said respective electrode pad by welding.

46. The method of claim 45, wherein arranging the electrode pads in a first arrangement comprises:
forming said electrode pads such that they are each arranged in the single longitudinal row and connected by a portion of conductive material.

47. The method of claim 46, further comprising:
following said step of applying a coating of electrically insulating material to said electrode structure, removing that portion of conductive material connecting each of said electrode pads, thereby separating each of the electrode pads.

48. The method of claim 47, wherein said wires are arranged such that they extend laterally from said electrode pads.

49. The method of claim 47, wherein said wires are arranged by extending each electrically conducting wire from its respective electrode pad at an angle relative to the single longitudinal row in which the electrode pads are arranged.

50. The method of claim 49, wherein securing the electrically conducting wires to said frame member comprises:
connecting the distal end of each wire to one or more sacrificial members.

51. The method of claim 50, wherein said distal end of said electrically conducting wires are welded to said one or more sacrificial members in a spaced apart arrangement to form said gap between adjacent electrically conducting wires.

52. The method of claim 51, wherein said one or more sacrificial members are in the form of a plate.

53. The method of claim 52, wherein each plate is made from a suitable material to facilitate welding of the distal end of the wire thereto.

54. An electrode structure formed using the method of claim 1.

55. A method of forming an electrode structure comprising a plurality of electrode pads and a plurality of electrically conductive wires extending from the electrode pads, for use in an electrode array of an implantable medical device, the method comprising:
attaching a sheet of conductive material to a sheet of carrier material to form a composite sheet;
working composite sheet to remove predetermined portions thereof to form a plurality of electrode pads of conductive material supported on an electrode support of carrier material, a frame member; and a plurality of electrically conductive wires, at least one electrically conductive wire connecting an electrode pad to the frame member;
coating said worked composite sheet with an electrically insulative material; and
removing said electrode support,
wherein the plurality of electrode pads are located in a single longitudinal row and the electrically conductive wires extend from alternate opposing ends or edges of adjacent electrode pads in the single longitudinal row, and wherein all of the electrode pads in the electrode structure are located in the single longitudinal row.

56. The method of claim 55, further comprising the step of:
removing said frame member.

57. The method of claim 55, wherein the step of attaching the sheet of conductive material to the sheet of carrier material is performed by roll bonding.

58. The method of claim 55, wherein the step of attaching the sheet of conductive material to the sheet of carrier material is performed by an adhesive.

59. The method of claim 55, wherein the sheet of conductive material is a sheet of platinum, iridium, gold, tungsten, tantalum, niobium, or an alloy with at least one of these metals.

60. The method of claim 55, wherein the sheet of carrier material is a plastics material.

61. The method of claim 55, wherein each electrically conductive wire connecting each electrode pad to said frame member is formed integral with the conductive material of said electrode pads and said frame member.

62. The method of to claim 55, wherein the step of coating the worked composite sheet with said electrically insulative material comprises:
spraying the relatively electrically insulative material over the worked composite sheet.

63. The method of claim 55, wherein the step of coating the worked composite sheet with said electrically insulating material comprises:
dipping the worked sheet into the relatively electrically insulative material.

64. The method of claim 55, wherein the step of removing said electrode support and said frame member comprises etching said carrier material from the conductive material and cutting the electrically conductive wires adjacent the frame member.

65. The method of claim 55, wherein the sheet of carrier material is a sheet of metal or alloy, such as copper or iron or their alloys.

66. The method of claim 65, wherein the metal or metal alloy is copper, iron or alloys thereof.

67. The method of claim 55, wherein prior to the coating step, portions of the worked composite sheet are masked to prevent coating the portions with said electrically insulative material.

68. The method of claim 67, wherein the masking is performed by applying a suitable tape or other suitable laminar material to the surface of the worked composite sheet.

69. The method of claim 55, wherein the step of coating the worked sheet with said electrically insulative material comprises:
   placing said worked sheet in a vapor deposition chamber; and
   depositing said electrically insulative material onto the worked sheet.

70. The method of claim 69, wherein the relatively electrically insulative material is parylene.

71. The method of claim 70, wherein the parylene is coated on the worked composite sheet via a vapour deposition polymerisation process.

72. The method of claim 55, wherein the composite sheet is worked via electrical discharge machining (EDM), etching or cutting, to remove portions of the sheet of electrical conductive material and/or the sheet of carrier material as desired.

73. The method of claim 72, wherein the frame member extends along an edge or edges of the composite sheet.

74. The method of claim 73, wherein the electrode support of carrier material extends between two sides of the frame member to provide structural integrity to the worked composite sheet.

75. The method of claim 74, wherein the electrode pads are formed along the surface of the electrode support of carrier material.

76. The method of claim 75, wherein each electrode pad is equally spaced from an adjacent electrode pad along the surface of the electrode support.

77. An electrode structure formed using the method of claim 55.

* * * * *